(12) United States Patent
Bishop et al.

(10) Patent No.: US 8,414,833 B2
(45) Date of Patent: Apr. 9, 2013

(54) MICRO-CHANNEL CHEMICAL CONCENTRATOR APPARATUS

(75) Inventors: David John Bishop, Summit, NJ (US); John VanAtta Gates, New Providence, NJ (US); Marc Scott Hodes, New Providence, NJ (US); Avinoam Komblit, Highland Park, NJ (US); Stanley Pau, Hoboken, NJ (US); Brijesh Vyas, Warren, NJ (US)

(73) Assignee: Alcatel Lucent, Paris (FR)

( * ) Notice: Subject to any disclaimer, the term of this patent is extended or adjusted under 35 U.S.C. 154(b) by 0 days.

(21) Appl. No.: 13/361,207

(22) Filed: Jan. 30, 2012

(65) Prior Publication Data

US 2012/0128546 A1 May 24, 2012

Related U.S. Application Data

(62) Division of application No. 11/784,783, filed on Apr. 9, 2007, which is a division of application No. 10/786,199, filed on Feb. 25, 2004, now Pat. No. 7,220,388.

(51) Int. Cl.
- *B01D 1/02* (2006.01)
- *B01D 63/08* (2006.01)
- *B01D 61/36* (2006.01)
- *B07C 1/02* (2006.01)

(52) U.S. Cl.
USPC ....... 422/105; 422/285; 210/744; 210/321.84

(58) Field of Classification Search .................. 422/100, 422/10, 285; 210/744
See application file for complete search history.

(56) References Cited

U.S. PATENT DOCUMENTS

| | | | | |
|---|---|---|---|---|
| 6,393,894 B1 * | 5/2002 | Bonne et al. | ................... | 73/23.2 |
| 6,607,644 B1 * | 8/2003 | Apffel, Jr. | ..................... | 204/451 |

OTHER PUBLICATIONS

Pursuant to 37 CFR 1.98(d)(1) Attached are Copies of Applicants' *Information Disclosure Statement* and Examiners' *Notices of Reference Cited* From the Grandparent Application, U.S. Appl. No. 10/786,199, filed Feb. 5, 2004 and Parent Application, U.S. Appl. No. 11/784,783, filed Apr. 9, 2007.

* cited by examiner

*Primary Examiner* — Krishnan S Menon
*Assistant Examiner* — Rebecca M Fritchman
(74) *Attorney, Agent, or Firm* — M. J. Urbano

(57) ABSTRACT

Apparatus and method for increasing the concentration of a chemical substance in a fluid comprise a micro-fluidic elongated channel formed in a substrate, with the channel being in fluid-flow communication with an ambient region along its elongated dimension. In general, the fluid includes first and second chemical substances having different vapor pressures. The apparatus includes an evaporation controller for increasing the evaporation rate of the fluid from the channel into the ambient region, thereby increasing the concentration of the lower vapor pressure (LVP) substance in the portion of the fluid remaining in the channel and increasing the concentration of the higher vapor pressure (HVP) substance in the portion of the fluid evaporated into the ambient region.

5 Claims, 3 Drawing Sheets

US 8,414,833 B2

MICRO-CHANNEL CHEMICAL CONCENTRATOR APPARATUS

CROSS-REFERENCE TO RELATED APPLICATIONS

This application is a division of prior application Ser. No. 11/784,783 filed on Apr. 9, 2007 entitled "Micro-Channel Chemical Concentrator," which is a division of prior application Ser. No. 10/786,199 filed on Feb. 25, 2004 (now U.S. Pat. No. 7,220,388).

BACKGROUND OF THE INVENTION

1. Field of the Invention

This invention relates to micro-channel chemical apparatus and methods for increasing the molar concentration of a chemical substance in a fluid.

2. Discussion of the Related Art

In some applications it is necessary that reactive agents, such as hydrogen peroxide, be used in a highly concentrated form. When highly concentrated, however, some reactive agents exhibit short shelf lives, which means that only limited quantities of the agent may be inventoried. In addition, some highly concentrated reactive agents may be unstable and/or unsafe.

Accordingly, there is a need in the art for a method and apparatus for maintaining such reactive agents in relatively dilute form and then concentrating them as needed.

In addition, it would be desirable for the apparatus to be realized in a miniaturized form, so as to make it more readily portable and reduce the expense of the concentrating process.

BRIEF SUMMARY OF THE INVENTION

In accordance with one aspect of our invention, apparatus for increasing the concentration of a chemical substance in a fluid comprises a micro-fluidic elongated channel formed in a substrate, with the channel being in fluid-flow communication with an ambient region along its elongated dimension. In general, the fluid includes first and second chemical substances having different vapor pressures. The apparatus includes an evaporation controller for increasing the evaporation rate of the fluid from the channel into the ambient region, thereby increasing the concentration of the lower vapor pressure (LVP) substance in the portion of the fluid remaining in the channel and increasing the concentration of the higher vapor pressure (HVP) substance in the portion of the fluid evaporated into the ambient region.

In accordance with another aspect of our invention, a method of altering the relative concentrations of first and second chemical substances having different vapor pressures in a fluid, comprises the steps of:

(a) introducing the fluid into an input port of an elongated micro-fluidic channel, the channel being in fluid-flow communication with an ambient region along its elongated dimension, (b) causing the fluid to flow along the channel and to exit from an output port, and (c) increasing the evaporation rate of the fluid from the channel into the ambient region, thereby increasing the concentration of the LVP substance in the portion of the fluid remaining in the channel and increasing the concentration of the HVP substance in the portion of the fluid evaporated into the ambient region.

In a preferred embodiment of both aspects of our invention, a gas-permeable membrane is disposed between the channel and the ambient region. The membrane confines the liquid form of the fluid to the channel but allows the evaporated portion to flow therethrough into the ambient region.

BRIEF DESCRIPTION OF THE SEVERAL VIEWS OF THE DRAWING

Our invention, together with its various features and advantages, can be readily understood from the following more detailed description taken in conjunction with the accompanying drawing, in which.

Figure 5:
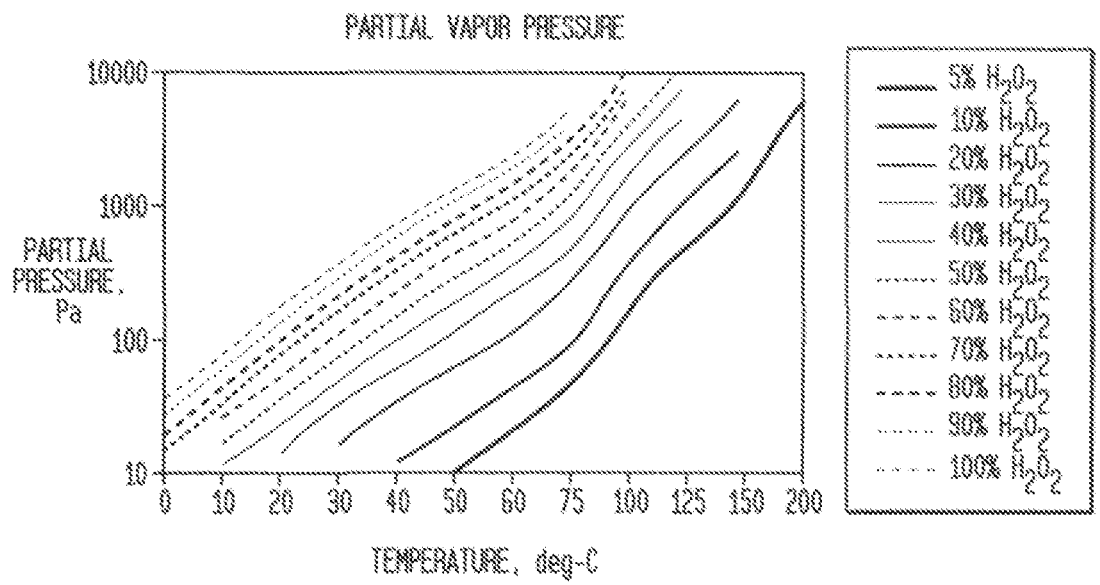
FIG. 5 is a graph showing how the partial vapor pressure of hydrogen peroxide ($H_2O_2$) in aqueous solutions varies with temperature at various $H_2O_2$ concentrations.
Figure 6:
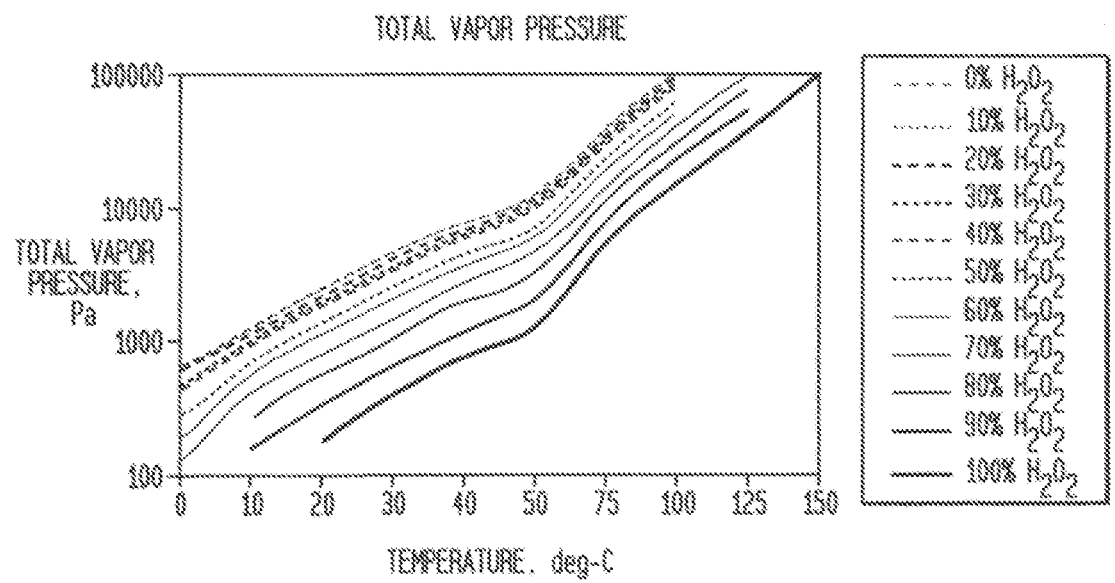
FIG. 6 is a graph showing how the total vapor pressure of hydrogen peroxide ($H_2O_2$) in aqueous solutions varies with temperature at various $H_2O_2$ concentrations.

The data of FIGS. 5-6 is taken from the website www.h2o2.com, which cites Van Laar, Z. Physik. Chem., Vo. 72, p. 723 (1910). The latter is incorporated herein by reference.

DETAILED DESCRIPTION OF THE INVENTION

Figure 1:
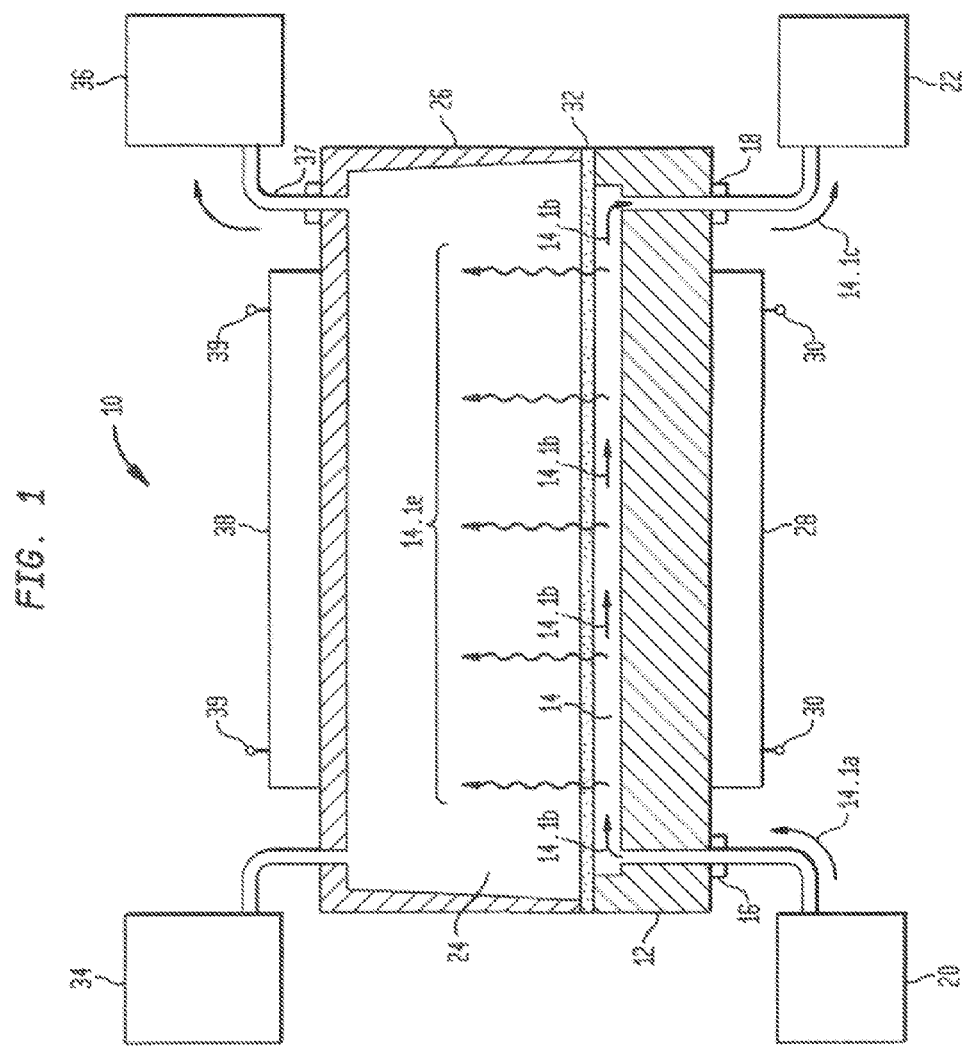
FIG. 1 is a schematic, cross sectional view of a micro-fluidic concentrator in accordance with an illustrative embodiment of our invention.
Figure 2:
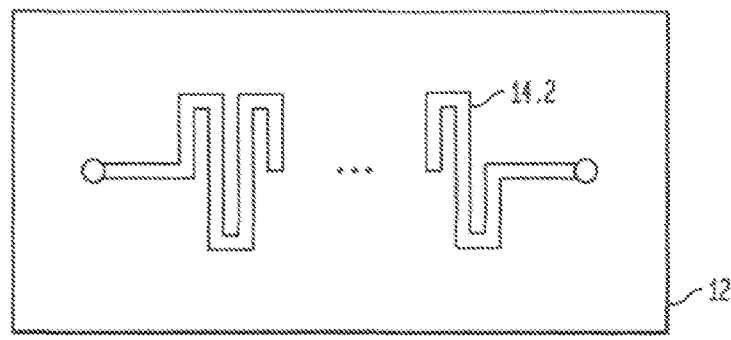
FIG. 2 is a schematic, top view of a serpentine or zigzag channel of the type depicted in the concentrator of FIG. 1.
Figure 3:
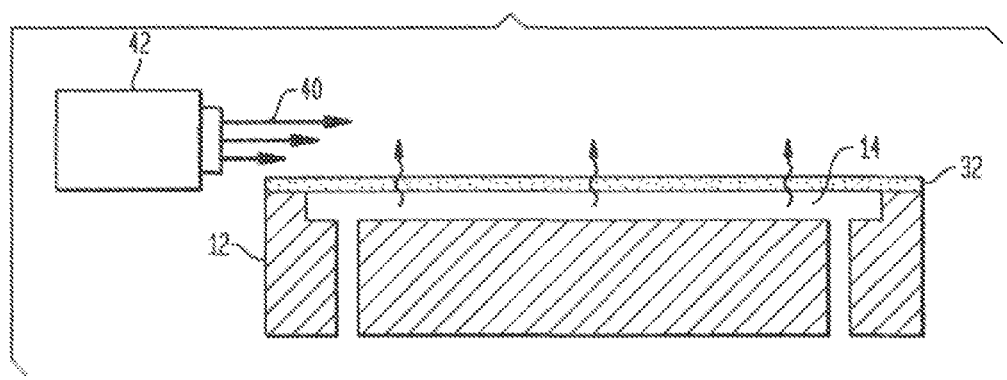
FIG. 3 is a schematic view of one technique for increasing the evaporation of substances from fluid in the channel of a concentrator in accordance with another embodiment of our invention.

In the following description we deal in general with a fluid that includes a HVP chemical substance and a LVP chemical substance. Turning now to FIG. 1, we show an illustrative embodiment of our invention, a micro-fluidic concentrator 10 for increasing the molar concentration of the substances by preferentially evaporating the HVP substance. Concentrator 10 comprises a substrate 12, an elongated fluid-flow channel 14 formed in the substrate 12, an input port 16 for allowing fluid 14.1a to be introduced from fluid source 20 into one end of channel 14, and an output port 18 for allowing fluid 14.1c to be extracted from another end of channel 14. The extracted fluid is passed to a utilization device 22, which, for example, may simply be a collection vessel.

Channel 14 is configured to be in fluid-flow communication with an ambient region 24, which in one embodiment is contained within a collection chamber 26. By fluid-flow communication we mean that gas or vapor 14.1e that evaporates from fluid 14.1b in channel 14 can flow directly or indirectly into region 24. By directly we mean that gas or vapor 14.1e evaporating from fluid 14.1b flows into region 24 without traversing any other components of the concentrator. On the other hand, by indirectly we mean that gas or vapor 14.1e evaporating from fluid 14.1b flows into region 24 but first traverses at least one other component of the concentrator. FIG. 1 illustrates the latter case; that is, a gas-permeable membrane 32 covers the top of channel 14 and serves several purposes: first, to confine the fluid to the channel, which in turn allows the fluid to be forced (e.g., pumped) through the channel, and second, to allow gas or vapor 14.1e to pass therethrough into chamber 24. In a preferred embodiment, the fluid 14.1 is a liquid, and the membrane 32 is permeable to gas but not to liquid. Illustratively, the membrane is made of a polymer (e.g., PDMS or a photoresist), a porous inorganic solid (e.g., porous silicon, which can be made by the well-known process of dissolving a single crystal silicon wafer in an electrochemical cell containing a hydrogen fluoride solution; in this process porosity can be tuned by varying the current applied to the cell), or a nanostructure of the type described, for example, by J. Kim et al., *IEEE Conf. MEMS*, Las Vegas, Nev., pp. 479-482 (January 2002), M. S. Hodes et al., copending U.S. patent application Ser. No. 10/674,448 filed on Sep. 30, 2003, and A. Komblit et al., copending U.S. patent application Ser. No. 10/403,159 filed on Mar. 31, 2003, all of which are incorporated herein by reference.

The concentrator 10 includes an evaporation controller for increasing the evaporation rate of the fluid 14.*b* from the channel 14 into the ambient region 24, thereby increasing the concentration of the LVP substance in the portion of the fluid 14.1*b* remaining in the channel and increasing the concentration of the HVP substance in the portion of the fluid evaporated into the ambient region. The evaporation rate may be enhanced in several ways in order to decrease the amount of time required to concentrate the LVP substance: for example, by heating the fluid, by lowering the pressure above the fluid in the channel, by flowing a gas over the fluid in order to minimize the vapor pressure of the LVP component in the ambient, and by proper design of the channel. These techniques may be applied singly or in any combination with one another and may be applied to those embodiments employing a gas-permeable membrane (as shown in FIG. 1) as well as to those that omit the membrane. In each of these techniques more of the HVP substance than the LVP substance evaporates into the ambient 24, which increases the concentration of the LVP substance in the portion of the fluid remaining in the channel and increases the concentration of the HVP substance in the portion of the fluid that evaporates from the channel into the ambient region.

Thus, the evaporation controller illustratively comprises a heater 28 thermally coupled to substrate 12, and hence to the fluid 14.1*b* in channel 14. The heater 28 is typically a thermoelectric module, and a suitable electronic controller (not shown) supplies electric current to electric terminals 30 to maintain the fluid temperature at the desired value. The heater may be operated in either a continuous or pulsed mode, as is well known in the art. In one embodiment of heating in a pulsed mode, the heater comprises a multiplicity of heating elements that are disposed along the length of the channel, and the heaters are pulsed in the sense that they are activated sequentially. Due to the density gradients it creates, pulsed mode heating also serves to mix the fluid.

The evaporation rate can also be increased by lowering the pressure in ambient region 24 or by blowing a gas over the liquid-vapor interface. For example, when ambient region 24 is contained within chamber 26, a vacuum may be established by using pump 34 to lower the pressure within the chamber. Alternatively, as shown in FIG. 3, the evaporation rate of the fluid in the channel is increased by flowing a gas 40 (air or an inert gas from source 42) directly across the surface of the channel 14 or across the surface of the membrane 32.

Finally, the evaporation rate may be increased by proper design of the shape of the channel 14. In particular, it is advantageous to increase the ratio of the surface area of the channel to its volume. Since the evaporation rate is known to be proportional to the area of the fluid surface from which evaporation is taking place (i.e., the surface area of the fluid exposed to ambient region 24), increasing the exposed surface area increases the evaporation rate. To this end, a preferred embodiment of our invention utilizes a serpentine or zigzag shape of the channel 14.2, as shown in FIG. 2. More specifically, the dimensions of channel 14 are determined by the evaporation rate per unit area of the injected liquid and the volume of required concentrated liquid per cycle.

Evaporation can occur in either a continuous or discrete cycle. In a continuous cycle, low molar liquid is injected and evaporated continuously, and high molar liquid is released at the output. In a discrete cycle, low molar liquid is injected into the channel, evaporated and then pushed out of the channel by a newer batch of liquid in a periodic cycle. Note that the liquid can also slowly be injected during the evaporation process to make up for the mass loss.

An evaporation cycle is taken to be the time required to increase the concentration of the HVP substance in the liquid phase to the desired value. In a flow system the required time corresponds to the residence time of a parcel of fluid flowing through the channel, but in a batch mode it corresponds to the time necessary for a batch of fluid to reach the desired HVP concentration when the fluid is flushed into the utilization device 22.

We assume that the decomposition of the fluid 14.1 is low at the exposed interface with ambient region 24 (e.g., at the interface between membrane 32 and fluid 14.1) and that the evaporation rate of the LVP substance is, as a practical matter, independent of its concentration. In general, we want to maximize the surface area for evaporation if the degradation of the fluid at the interface is low. Given, the evaporation rate and the desired concentration of the LVP substance at the output port 18, one skilled in the art can readily calculate the exposed area of the channel 14 (e.g., the top surface area of the serpentine channel 14.2 shown in FIG. 2) and the duration of the evaporation cycle. Designing channel 14 to have a serpentine geometry allows for uniform heating and cooling of the fluid 14.1 by providing a large contact area between the fluid and the substrate.

The length of the channel and its cross sectional area determine the volume of fluid that can be concentrated at any one particular time. The channel length on the other hand is determined in part by the size of the substrate surface in which the channel is formed. In designs that utilize relatively expensive substrates, such as silicon, overall cost considerations come into play when deciding whether to increase the size of the substrate in order to realize longer channels. In those embodiments that employ collection chamber 24, it may be desirable to condense the gas or vapors 14.1*e* of the evaporant, which includes an increased concentration of the HVP substance. In one embodiment, condensation is achieved by means of a cooler 38 thermally coupled to chamber 24. The condensate is collected and stored in reservoir 36. Illustratively, the cooler is a thermoelectric cooler driven by an electronic controller (not shown) that supplies current to electric terminals 39. Other forms of coolers well known in the art may also be utilized. Alternatively, the cooler may be positioned proximate the exit conduit 37, so that condensation takes place primarily in the conduit 37 rather than in the chamber 24. Another design of this embodiment is shown in FIG. 4, which will be discussed infra.

To illustrate the operation, let us assume that the fluid 14.1 is a liquid, which is in dilute form (14.1*a*) when introduced into the channel 14 via input port 16 but is in concentrated form (14.1*c*) when extracted from output port 18. By dilute and concentrated we mean that the molar concentration of the LVP substance is higher at the output port than at the input port. The liquid in the channel 14 is then heated to a temperature below its boiling point to stimulate evaporation of the liquid from the channel 14 into the ambient region 24, thereby increasing the concentration of the LVP substance in the liquid remaining in the channel. Temperatures above the boiling point are preferably avoided in order to prevent bubble formation, which might clog the channel and to prevent thermal breakdown of the chemical substances in the fluid. Next, the concentrated liquid is cooled (e.g., to room temperature), and the liquid is flushed from the channel into utilization device 22. Flushing may be achieved by forcing air or another liquid into the input port 16 or by using a mechanical plunger.

The electronic controller mentioned earlier may be employed to control not only the current supplied to the heater, 28 and the cooler 38, but also to control any sensors (e.g., those that sense fluid temperature), pumps or fluid sources coupled to the concentrator, etc.

Figure 4:
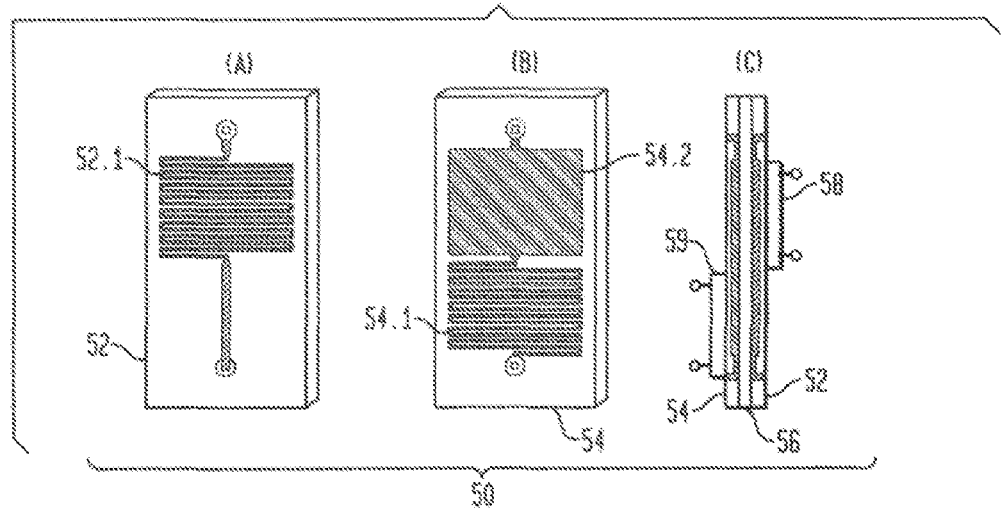
FIG. 4 is a schematic, exploded view of a concentrator in accordance with yet another embodiment of our invention.

Another embodiment of our micro-channel chemical concentrator 50 is shown in FIG. 4. Here, the concentrator 50 includes a heating layer 52 having a serpentine channel 52.1 and a heater 58 (FIGS. 4A and 4C), a cooling layer 54 having a serpentine channel 54.1 and a cooler 59, as well as a collection cavity 54.2 in fluid-flow communication with channel 54.1 (FIGS. 4B and 4C). A gas permeable membrane 56 is disposed between the heater layer 52 and the cooling layer 54. Preferably, the heater 58 and the cooler 59, as well as their associated channels 52.1 and 54.1, respectively, are axially separated from one another so that there is no (or very little) overlap between them, thereby reducing the likelihood that the heating and cooling steps will interfere with one another.

The heater 58 is positioned adjacent the channel 52.1. It may comprise a resistive heater built into layer 52, or it may comprise heat tape attached to the surface of layer 52. Likewise, the cooling layer 54 comprises a channel 54.1 for cooling the fluid, and/or it may include an external cooler 59 positioned adjacent the channel 54.1.

In this embodiment of our invention, the liquid substance, which is to be concentrated, has a higher vapor pressure than the solvent liquid. A portion of the liquid is evaporated from the heater layer 52, passes through a membrane 56, and enters the cooling layer 54, where the evaporated portion is condensed and collected in cavity 54.2.

Illustrative Application

High molar hydrogen peroxide ($H_2O_2$) is a perishable and reactive chemical, which has a limited shelf life. A low molar concentration of $H_2O_2$ is desirable because in this form the chemical is more durable and transportable, as well as safer than at higher molar concentrations. For many applications, where a higher molar concentration of $H_2O_2$ is needed, it is desirable to convert a low molar concentration to a high molar concentration at or near the time when the chemical is to be used.

The illustrative application that follows describes increasing the concentration of $H_2O_2$ in an aqueous solution. Thus, in the terminology of the previous description the fluid 14.1 is a liquid, the HVP substance is water, and the LVP substance is $H_2O_2$. Various materials, dimensions and operating conditions are provided by way of illustration only and, unless otherwise expressly stated, are not intended to limit the scope of the invention.

More specifically, our calculations show that our microchannel concentrator can be used to distill hydrogen peroxide from, for example, a 3% molar concentration to a >10% molar concentration in time scales on the order of a few minutes. We considered conversion of 1 microliter or 1 $mm^3$ of liquid. An illustrative channel is, for example, 500 µm wide, 250 µm deep and 8 mm long. In this case, the surface area of the channel is 4 $mm^2$, but it can have an arbitrary footprint in practice. FIGS. 5-6 show the partial and total vapor pressures, respectively, of $H_2O_2$ as a function of temperature for different concentrations. In general, the vapor pressure of $H_2O_2$ is more than ten times smaller than that of water. By heating an aqueous solution of $H_2O_2$, water is preferentially evaporated into air (i.e., into ambient region 24), resulting in a more concentrated $H_2O_2$ solution at output port 18. Assuming we start with a 10% $H_2O_2$ solution, only about 1% of the vapor 14.1e is $H_2O_2$, which means that there is little loss of $H_2O_2$ in the concentrating process for solutions that initially have low concentrations of $H_2O_2$.

We know that the evaporation rate for $H_2O_2$ increases exponentially with increase in temperature and linearly with increase in the concentration in the liquid at any temperature. The loss of $H_2O_2$ is found to be approximately 10% of the concentration of $H_2O_2$ in solution at concentrations of interest and temperatures below the boiling point of the solution. So long as the LVP component of the fluid has a smaller vapor pressure than the HVP component of the fluid, evaporation is favorable insofar as concentrating the LVP component. In the $H_2O_2$—$H_2O$ example this implies we can concentrate $H_2O_2$ far beyond 10 wt % in solution.

It is to be understood that the above-described arrangements are merely illustrative of the many possible specific embodiments that can be devised to represent application of the principles of the invention. Numerous and varied other arrangements can be devised in accordance with these principles by those skilled in the art without departing from the spirit and scope of the invention. In particular, it may be useful to coat the walls of the channel for any number of reasons; e.g., to prevent corrosion or degradation of the channel; to prevent the formation of bubbles in the fluid and hence to prevent clogging; or to improve thermal conductivity. For example, in the designs where the channel is formed in a silicon substrate and a solution of $H_2O_2$—$H_2O$ is to be concentrated, we know that $H_2O_2$ attacks silicon and would degrade the channel, so we need to coat the silicon channel with a layer of protective material such as silicon dioxide.

We claim:

1. An apparatus comprising:
    a first substrate including a first fluid-flow channel having a serpentine portion in a first section of said first substrate;
    a second substrate including a fluid-flow second channel having a serpentine portion and a cavity; said cavity being positioned in a first section of said second substrate and adjacent to said serpentine portion of said first channel;
    a gas permeable membrane disposed between said first and the second substrates,
    a heater positioned on said first section of said first substrate, adjacent to said serpentine portion of said first channel, and configured to evaporate a portion of the fluid in said serpentine portion of said first channel, said evaporated portion passing through said membrane into said cavity; and
    a cooler positioned on said second substrate, adjacent to said serpentine portion of said second channel, and configured to cool said evaporated fluid portion in said serpentine portion of said second channel.

2. The apparatus of claim 1, further including a coating formed on the surfaces of said channels.

3. The apparatus of claim 1, wherein said heater includes a heating layer disposed in said first substrate and said cooler includes a cooling layer disposed in said second substrate.

4. The apparatus of claim 1, wherein said heater is disposed toward said one end of said first substrate and said cooler is disposed toward said opposite end of said second substrate.

5. The apparatus of claim 1, wherein said first and second channels comprise micro-channels.

* * * * *